United States Patent [19]

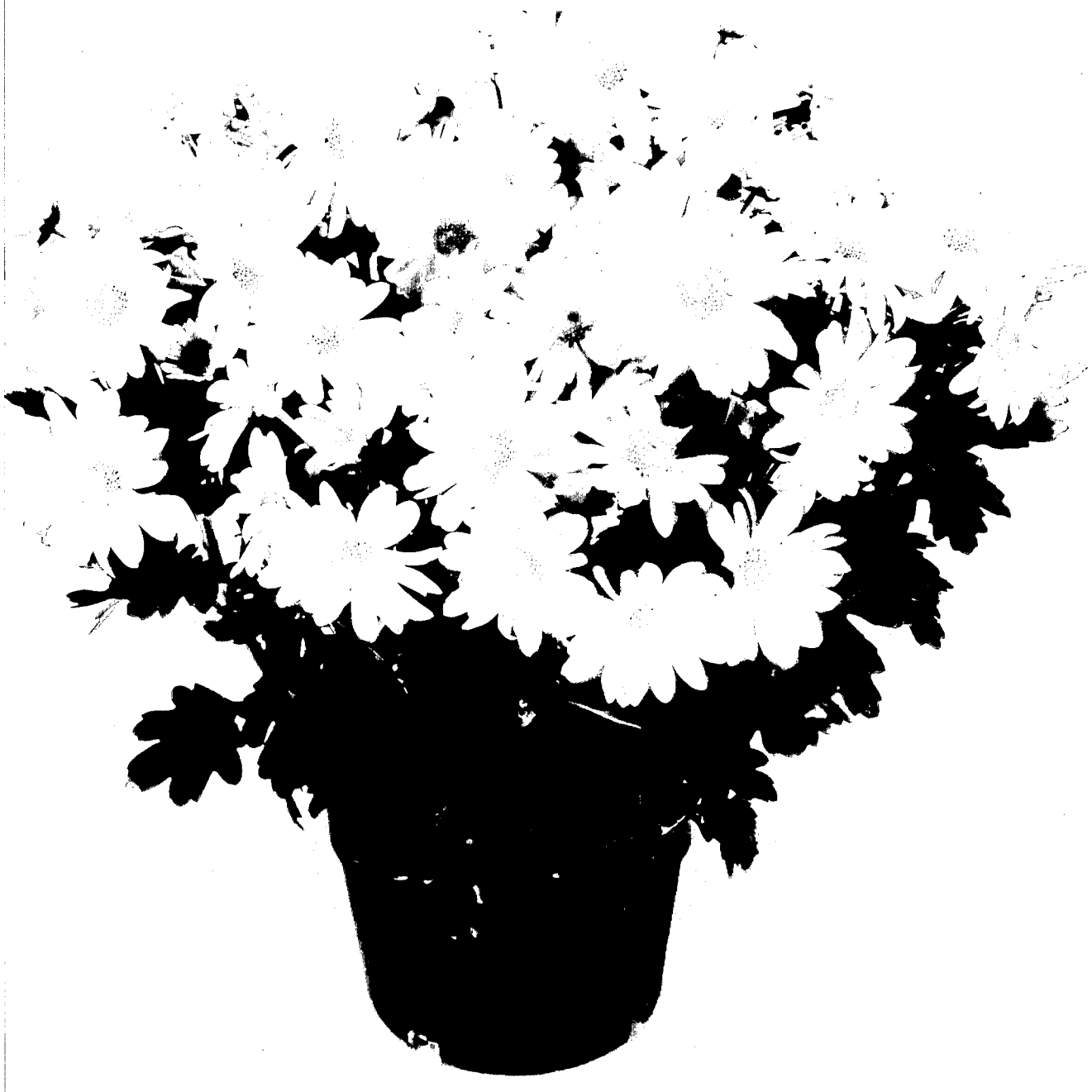

Shoesmith, deceased

[11] Patent Number: Plant 5,778

[45] Date of Patent: Aug. 12, 1986

[54] CHRYSANTHEMUM PLANT NAMED BRIGHTLIGHT

[75] Inventor: Leonard H. Shoesmith, deceased, late of Woking Surrey, England, by May Victoria Shoesmith, executrix

[73] Assignee: Ball PanAm Plant Company, Parrish, Fla.

[21] Appl. No.: 603,840

[22] Filed: Apr. 25, 1984

[51] Int. Cl.[3] ..... A01H 5/00

[52] U.S. Cl. ..... Plt./74

[58] Field of Search ..... Plt./74

*Primary Examiner*—James R. Feyrer

*Attorney, Agent, or Firm*—Schwartz, Jeffery, Schwaab, Mack, Blumenthal & Evans

[57] ABSTRACT

A new and distinct cultivar of chyrsanthemum plant named Brightlight characterized by its flat capitulum form and single capitulum type, bright yellow ray floret color, excellent flower substance, diameter of 55–65 cm. across face of capitulum, medium pot height, and semi-upright branching pattern.

1 Drawing Figure

The present invention comprises a new and distinct cultivar of *Chrysanthemum morifolium,* Ramat., named Brightlight.

Brightlight is a product of a planned breeding program which had the objective of creating new chrysanthemum cultivars with single capitulum type, bright yellow ray floret color, good flower substance, 8 week flowering response, and ability to produce commercially acceptable quality year round. Such traits in combination were not present in previously available commercial cultivars.

Brightlight was originated from a hybridization made in a controlled breeding program in Westfield, Woking England in 1978. The male and female parents are unknown at this time. Brightlight was discovered and selected as one flowering plant within the progeny of the stated parentage by Leonard H. Shoesmith on November, 1979 in a controlled environment in West Chicago, Ill. and given the code name P9-1261-YS.

The first act of asexual reproduction of Brightlight was accomplished when vegetative cuttings were taken from the initial selection on February 1980 in a controlled environment in West Chicago, Ill. by a technician working under formulations established and supervised by Leonard H. Shoesmith. Horticultural examination of selected units initiated March 1980 has demonstrated that the combination of characteristics as herein disclosed for Brightlight are firmly fixed and are retained through successive generations of asexual reproduction.

Brightlight has not been observed under all possible environmental conditions. The phenotype may vary significantly with variations in environment such as temperature, light intensity, and day length. The following observations, measurements and comparisons describe plants grown in West Chicago, Ill. and Parrish, Fla. under greenhouse conditions which approximate those generally used in commercial practice.

The following traits have been repeatedly observed and are determined to be basic characteristics of Brightlight, which in combination distinguish this chrysanthemum as a new and distinct cultivar:

(1) Flat capitulum form.

(2) Single capitulum type.

(3) Bright yellow ray floret color.

(4) Excellent flower substance.

(5) Diameter of 55–65 cm. across the face of the capitulum.

(6) Medium pot plant height of about 300 mm. from edge of pot. Applications of B-9 may be used to control plant height.

(7) Semi-upright branching pattern.

Of the many commercial cultivars known to the present inventor, the most similar in comparison to Brightlight is Pert, disclosed in U.S. Plant Pat. No. 4,764, granted Sept. 8, 1981. In comparison to Pert, Brightlight has lighter yellow flower color, a slightly smaller flower, is one week earlier in response and has better performance than Pert at high temperatures, that is 90° F. day and 75° F. night. The flower type and plant habit are similar to those same characteristics of Pert.

The accompanying photographic drawing shows typical inflorescence and foliage characteristics of Brightlight. The photograph is in black and white except for a cluster of flowers which represent the true flower color of Brightlight.

In the following description color references are made to The Royal Horticultural Society Colour Chart. The color values were determined between 10:30–11:00 A.M. on Aug. 19, 1983 under 7000 ft. candles of natural light at Parrish, Fla.

Classification:

*Botanical.*—*Chrysanthemum morifolium,* Ramat., cv Brightlight.

*Commercial.*—Daisy pot mum.

I. Inflorescence:

A. *Capitulum.*—Form: flat. Type: Daisy. Diameter Across Face: 55–65 mm.

B. *Corolla of ray florets.*—Color (General Tonality From A Distance of Three Meters): Bright yellow. Color (under surface): 4B. Color (Upper surface): 2A.

C. *Corolla of disc florets.*—Color (mature): Yellow. Color (immature): Greenish-yellow.

D. *Reproductive organs.*—Androecium: Present in disc floret only; abundant. Gynoecium: Present in both ray and disc florets; abundant.

II Plant:

A. *General Appearance.*—Height: Upright, 300 mm. at flowering with one application of B-9.

B. *Foliage.*—Color (abaxial): 147B. Color (adaxial): 147A. Shape: Deeply lobed and somewhat serrated.

I claim:

1. A new and distinct cultivar of chrysanthemum plant named Brightlight, as illustrated and described, and particularly characterized by its flat capitulum form and single capitulum type, bright yellow ray floret color, excellent flower substance, diameter of 55–65 cm. across face of capitulum, medium pot height, and semi-upright branching pattern.

* * * * *